United States Patent [19]

Scott et al.

[11] 4,289,708

[45] Sep. 15, 1981

[54] CATALYST METAL SEPARATION FROM SATURATED ALIPHATIC MONOCARBOXYLIC ACIDS

[75] Inventors: Robert H. Scott; Hubert H. Thigpen, both of Corpus Christi; Frank Wood, Jr., Houston, all of Tex.

[73] Assignee: Celanese Corporation, New York, N.Y.

[21] Appl. No.: 65,239

[22] Filed: Aug. 9, 1979

[51] Int. Cl.$^3$ .................... C07C 51/235; C07C 55/07; C07C 53/122; C07C 53/127
[52] U.S. Cl. .................................. 260/413; 252/413; 562/531; 562/597
[58] Field of Search ................ 252/413; 260/413 N, 260/438.1, 429 R; 562/531, 536, 549, 597; 423/50

[56] References Cited

U.S. PATENT DOCUMENTS

| | | | |
|---|---|---|---|
| 2,828,337 | 3/1958 | Whitaker | 260/413 |
| 3,492,340 | 1/1970 | Aguilo et al. | 252/413 |
| 3,840,469 | 10/1974 | Hobbs, Jr. et al. | 252/413 |
| 4,008,306 | 2/1977 | Yamashita | 423/50 |

FOREIGN PATENT DOCUMENTS 52-33614  3/1977  Japan .

*Primary Examiner*—P. E. Konopka
*Attorney, Agent, or Firm*—Linn I. Grim

[57] ABSTRACT

A process is described for separating soluble copper and manganese catalysts from organic saturated monocarboxylic acids having 3 to 9 carbon atoms by precipitating the copper and manganese as oxalates.

6 Claims, No Drawings

CATALYST METAL SEPARATION FROM SATURATED ALIPHATIC MONOCARBOXYLIC ACIDS

BACKGROUND OF THE INVENTION

In the production of organic saturated aliphatic monocarboxylic acids having 6 to 9 carbon atoms by oxidation of the corresponding aldehydes, soluble manganese and copper compounds, such as manganous acetate and cupric acetate, are used in combination as catalysts to provide high carbon conversion and high efficiency of aldehyde to acid. High carbon conversion and high efficiency are essential not only to provide the good yeilds of acids but also to produce relatively small amounts of undesirable by-products and thus avoid recycling unreacted starting materials. The oxidation reaction can be conducted in the liquid phase using a single stage or multiple stage reactors. These reactions can be operated under pressure in the range from about 60 to about 150 pounds per square inch gauge, preferably from about 85 to about 95 pounds per square inch gauge, with air or oxygen containing gas in the temperature range from about 50° C. to about 80° C. Such a process is described in copending application U.S. Ser. No. 065,241 filed Aug. 9, 1979 assigned to the same assignee and filed concurrently with this application.

However, it has been found that metallic copper will precipitate from acids prepared using such mixed soluble catalyst compounds due to reduction during the processing of these acids, especially during distillation. The presence of precipitated copper particles in turn can lead to serious mechanical problems such as reboiler fouling and erosion of pump impellers. Manganese compounds, on the other hand, tend to remain soluble and are not readily reduced to the metal.

Removing the soluble metal catalysts from the acid products would not only avoid the aforementioned mechanical problems but would also provide purer acid products. As has been described in copending application U.S. Ser. No. 065,240 filed Aug. 9, 1979 U.S. Pat. No. 4,246,185 assigned to the same assignee and filed concurrently with this application, the copper and manganese from soluble catalysts can be precipitated from organic saturated aliphatic monocarboxylic acids having 6 to 9 carbon atoms by the addition of aqueous oxalic acid. This procedure utilizes water as a separation means for the precipitated metal oxalates, since the organic acids, being substantially insoluble in water, form a separate organic phase from the aqueous phase containing the precipitated metal oxalates. The resulting organic acids which have been rendered substantially free of manganese and copper then can be readily decanted from the aqueous phase, and need not be filtered. However, using aqueous oxalic acid to remove copper and manganese from lower organic saturated aliphatic monocarboxylic acids containing 2 to 5 carbon atoms is not economically feasible since these acids are soluble in water, and following the addition of the aqueous oxalic acid the resulting solution would have to be distilled to recover the desired acid products.

In the prior art, there are various techniques to describe the removal of metal catalysts from the reaction product. In U.S. Pat. No. 3,840,469, there is a disclosure for the cobalt catalyst recovery from an acetic acid medium derived from the liquid phase oxidation of aliphatic hydrocarbons. This procedure precipitates the cobalt as cobalt oxalate in the acetic acid product. The patent indicates that manganese would not undergo precipitation in this procedure. In U.S. Pat. No. 2,380,731, a procedure is described using oxalic acid to remove numerous metals such as iron, magnesium, chromium, copper, vanadium etc. from a refractory inorganic support such as a clay or alumina or silica or an alumina-silica refractory catalytic cracking catalyst. These procedures are not related to the process of this invention.

SUMMARY OF THE INVENTION

The present invention provides a simple means for separating manganese and copper from organic saturated aliphatic monocarboxylic acids having 3 to 9 carbon atoms. This is accomplished by adding to organic acids containing soluble metal catalysts a sufficient amount of oxalic acid to precipitate the copper and manganese as their oxalates. The precipitated oxalates then can be separated from the organic acids by filtration or centrifugation, and preferably by continuous centrifugation. The resulting organic acids then can be purified further by distillation.

The organic acids subjected to the separation process of this invention are derived from the oxidation of their corresponding aldehydes using catalytic amounts of a mixture soluble manganese and copper catalysts, such as manganous acetate and cupric acetate, which are soluble in the acid product, and will contain from 3 to 9 carbon atoms. These acids include propanoic, butanoic, pentanoic, hexanoic, heptanoic, octanoic and nonanoic acids. Water will preferably not be used when separating the precipitated metal oxalates from organic acids containing 3 to 5 carbon atoms, since these acids are soluble in water and distillation would have to be employed to separate water from acid. Organic acids containing 6 to 9 carbon atoms, however, are substantially insoluble in water, and can be purified following the addition of oxalic acid in the manner described in copending application U.S. Ser. No. 065,240 filed Aug. 9, 1979 U.S. Pat. No. 4,246,185.

The amount of oxalic acid present in the organic acids should be sufficient to precipitate most of the soluble manganese and copper catalysts from the organic acids. Preferably at least a stoichiometric amount of oxalic acid to metal catalysts should be used, and it is desirable to use an excess of oxalic acid to assure complete precipitation. For example, excesses of 2 to 1000 percent oxalic acid can be used, if desired.

The invention will be illustrated by the following examples.

EXAMPLE 1 n-Heptanoic acid (22,982 grams) produced by the oxidation of n-heptanal in the presence of a catalyst consisting of a combination of cupric acetate and manganous acetate (300 parts per million copper and 300 parts per million manganese) was combined at ambient temperatures with 32.63 grams of oxalic acid (10% excess of oxalic acid to copper and manganese on a mole to mole basis). After stirring for 9 hours, cupric and manganous oxalates precipitate from the heptanoic acid, settled and were filtered, leaving clear substantially metal-free heptanoic acid.

EXAMPLE 2

The procedure of Example 1 was followed in every respect but one, the heptanoic acid containing the oxalate precipitates centrifuged. Clear, substantially metal-free heptanoic acid was recovered.

EXAMPLE 3 n-Nonanoic acid (22,826 grams) produced by the oxidation of n-nonanal in the presence of a catalyst consisting of a combination of cupric acetate and manganous acetate (300 parts per million each of copper and manganese) was combined at room temperature with 32.41 grams oxalic acid (10% excess of oxalic acid to copper and manganese) and stirred for 10 hours. Cupric and manganous oxalates, precipitated from the nonanoic acid, settled and were filtered, leaving clear substantially metal-free nonanoic acid.

In addition to the acids disclosed in the foregoing examples, copper and manganese metals can be separated from other acids such as propanoic acid, butanoic acid, pentanoic acid, hexanoic acid, and octanoic acid.

The preferred technique of removing soluble copper and manganese catalysts from higher carbon (6–9) containing monocarboxylic acids as described and claimed in copending application U.S. Ser. No. 065,240 filed Aug. 9, 1979 U.S. Pat. No. 4,246,185 is described in Examples 4–6.

EXAMPLES 4–6 n-Heptanoic acid produced by the oxidation of n-heptanal in the presence of a catalyst consisting of a combination of copper acetate and manganese acetate (330 parts per million copper and 295 parts per million manganese) was combined at ambient temperatures with an excess of oxalic acid to the copper and manganese present (on a mole to mole basis). The oxalic acid was added as an aqueous solution. The volume ratio of heptanoic acid present to the water in the aqueous oxalic acid can range from 1.7/1 to 9.2/1. Two phases, an organic acid phase and an aqueous phase, form. The copper and manganese oxalates oxalates precipitate from the organic acid phase into the aqueous phase, and the precipitated oxalates subsequently settled. The time required for the organic and aqueous phases to form decreased as the organic acid to water volume ratio decreased. Table I illustrates the results utilizing an organic acid to water volume ratio of 1.7.

TABLE I

| Example | Organic Product | Organic Acid: Water Volume Ratio | % Excess of Stoichiometric Amounts of Oxalic Acid to Metals | Organic Phase Copper % Removal | Mn % Removal | Initial Phasing Time |
|---|---|---|---|---|---|---|
| 4 | heptanoic acid 330 ppm Cu and 295 ppm Mn | 1.7 | 2 | 99.9 | 99.6 | ~3 minutes |
| 5 | heptanoic acid 330 ppm Cu and 295 ppm Mn | 1.7 | 10 | 99.9 | 99.9 | ~3 minutes |
| 6 | nonanoic acid 400 ppm Cu and 360 ppm Mn | 1.7 | 10 | 99.9 | 99.9 | ~2 minutes |

What is claimed is:

1. A process for separating manganese and copper from organic saturated aliphatic monocarboxylic acids having 3 to 9 carbon atoms which comprises treating said metal-containing organic acids with oxalic acid, in an amount sufficient to precipitate sebstantially all of the copper and manganese as cupric oxalate and manganous oxalate, and separating siad oxalates from said acids.

2. The process of claim 1 wherein said oxalates are filtered from said acids.

3. The process of claim 1 wherein said oxalates are separated from said acids by centrifugation.

4. In a process of oxidizing saturated aliphatic aldehydes having 3 to 9 carbon atoms to their corresponding acids using soluble copper and manganese catalysts, the improvement comprising adding sufficient oxalic acid to the metal-containing organic acid product to precipitate substantially all of the copper and manganese to cupric oxalate and manganous oxalate and separating said oxalates from said acids.

5. The process of claim 4 wherein said acid is heptanoic acid.

6. The process of claim 4 wherein said acid is nonanoic acid.

* * * * *

UNITED STATES PATENT AND TRADEMARK OFFICE
CERTIFICATE OF CORRECTION

PATENT NO. : 4,289,708
DATED : September 15, 1981
INVENTOR(S) : ROBERT H. SCOTT ET AL It is certified that error appears in the above-identified patent and that said Letters Patent are hereby corrected as shown below:

Column 1, line 15, delete "yeilds" and insert ---yields---.

Column 4, line 3, delete "oxalates" in the first instance since the word is duplicated.

Column 4, claim 1, line 35, delete "sebstantially" and insert ---substantially---.

Column 4, claim 1, line 37, delete "siad" and insert ---said---.

Signed and Sealed this

Twenty-fourth Day of November 1981

[SEAL]

Attest:

GERALD J. MOSSINGHOFF

Attesting Officer    Commissioner of Patents and Trademarks